United States Patent
Exner et al.

(10) Patent No.: US 6,686,162 B2
(45) Date of Patent: Feb. 3, 2004

(54) **OLIGONUCLEOTIDES AND METHODS FOR DETECTING *BORRELIA BURGDORFERI***

(75) Inventors: Maurice Exner, Mission Viejo, CA (US); Hasnah Hamdan, Riverside, CA (US); Michael Lewinski, San Clemente, CA (US)

(73) Assignee: Quest Diagnostics Investments, Incorporated, Wilmington, DE (US)

( * ) Notice: Subject to any disclaimer, the term of this patent is extended or adjusted under 35 U.S.C. 154(b) by 181 days.

(21) Appl. No.: 10/011,340

(22) Filed: Dec. 4, 2001

(65) Prior Publication Data

US 2003/0108875 A1 Jun. 12, 2003

(51) Int. Cl.$^7$ ................................................ C12Q 1/68
(52) U.S. Cl. ....................................................... 435/6
(58) Field of Search ............................. 536/23.1, 24.3; 435/91.2, 6

(56) References Cited

U.S. PATENT DOCUMENTS

| | | |
|---|---|---|
| 5,538,848 A | 7/1996 | Livak et al. |
| 5,723,591 A | 3/1998 | Livak et al. |
| 6,028,290 A | 2/2000 | Yasuhara et al. |
| 6,060,240 A | 5/2000 | Kamb et al. |
| 6,150,107 A | 11/2000 | Glazer et al. |
| 6,297,016 B1 | 10/2001 | Egholm et al. |
| 6,316,230 B1 | 11/2001 | Egholm et al. |
| 6,316,610 B2 | 11/2001 | Lee et al. |

FOREIGN PATENT DOCUMENTS

| | | | |
|---|---|---|---|
| EP | 0 656 955 B1 | * | 1/1998 |
| WO | WO 92/07957 | * | 5/1992 |

OTHER PUBLICATIONS

Benach et al., "Spirochetes Isolated from the Blood of Two Patients with Lyme Disease," *N. Engl. J. Med.* 308: 740–742, 1983.

Chu et al., "Postsynthesis Functionalization of Oligonucleotides," in *Protocols for Oligonucleotide Conjugates, Methods Mol. Biol.* 26:145–165, 1994.

Hafner et al., "Isothermal Amplification and Multimerization of DNA Bst DNA Polymerase," *Biotechniques* Apr. 2001;30(4):852–6, 858, 860 passim.

Hileman et al., "Synthesis and Characterization of Conjugates Formed between Periodate–Oxidized Ribonucleotides and Amine–Containing Flourophores," *Bioconjug. Chem.* 5, 436–444, 1994.

Liebling et al., "The Polymerase Chain Reaction for the Detection of *Borrelia burgdorferi* in Human Body Fluids," *Arth Rheum* 36(5): 665–675, 1993.

Saiki, "Amplification of Genomic DNA" in *PCR Protocols*, Innis et al., Eds., *Academic Press*, San Diego, CA 1990, pp 13–20.

Schmidt et al., "Detection of *Borrelia burgdorferi* DNA by Polymerase Chain Reaction in the Urine and Breast Milk of Patients with Lyme Borreliosis," *Diagn. Microbiol. Infect. Dis.* 21:121–128, 1995.

Schwaiger et al., "Routine diagnosis of *Borrelia burgdorferi* (sensu lato) infections using a real–time PCR assay" *Clin. Microbiol. Infect.* 7(9): 461–9, 2001.

van Schie et al., "Semiautomated Clone Verification by Real–Time PCR Using Molecular Beacons," *Biotechniques* 29:1296–1308, 2000.

Wharam et al., "Specific Detection of DNA and RNA targets using a novel isothermal nucleic acid amplification assay based on the formation of a three–way junction structure," *Nucleic Acids Res.* Jun. 1, 2001; 29(11):E54–E54.

Zhong, et al. "Visualization of oligonucleotide probes and point mutations in interphase nuclei and DNA fibers using rolling circle DNA amplification" *Proc. Natl. Sci. USA* Mar. 27, 2001;98(7):3940–3945.

* cited by examiner

Primary Examiner—Jeffrey Fredman
Assistant Examiner—Teresa Strzelecka
(74) *Attorney, Agent, or Firm*—Foley & Lardner; Richard J. Warburg

(57) ABSTRACT

The present invention provides methods and compositions for determining the presence and/or amount of *Borrelia burgdorferi* nucleic acids in a test sample related to Lyme disease. In particular, substantially purified oligonucleotide primers and probes are described that can be used for qualitatively and quantitatively detecting *Borrelia burgdorferi* nucleic acid in a test sample by amplification methods. The present invention also provides primers and probes for generating and detecting control nucleic acid sequences that provide a convenient method for assessing internal quality control of the *Borrelia burgdorferi* assay.

1 Claim, No Drawings

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttgcaaatct tttctctggt g                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agaattaact ccgccttgag a                                               21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccttcctgtt gaacccctc ttgaac                                           26

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cttgtaccag ttgtacggtc c                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggtagcagcg gtagagttgt a                                               21

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

-continued

```
atcatgatgt tcaagttgtg ttttgc                                      26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccttcctgtt gaacaccctc ttgaac                                      26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcatgatgt tcaagttgtg ttttgc                                      26
```

US 6,686,162 B2

OLIGONUCLEOTIDES AND METHODS FOR DETECTING *BORRELIA BURGDORFERI*

FIELD OF THE INVENTION

The present invention relates generally to compositions and methods for detecting nucleic acids for the organism *Borrelia burgdorferi* in a test sample.

BACKGROUND OF THE INVENTION

The following discussion of the background of the invention is merely provided to aid the reader in understanding the invention and is not admitted to describe or constitute prior art to the present invention.

Lyme disease, also known as Lyme borreliosis, is a tick-transmitted, spirochetal, inflammatory disorder causing a rash (erythema [chronicum] migrans) that may be followed weeks to months later by neurologic, cardiac, or joint abnormalities. Lyme disease was recognized in 1975 because of close clustering of cases in Lyme, Conn. It has since been reported in many states in USA and numerous foreign countries.

Lyme disease has been the most commonly reported tick-borne illness in the USA. It is caused by a spirochete, *Borrelia burgdorferi*, transmitted primarily by minute ticks of the *ixodes ricinus* complex. Once attached to the skin, they continue to engorge on blood for days. Transmission of *Borrelia burgdorferi* does not usually occur until the infected tick has been in place for at least 36 to 48 hrs; thus, screening for ticks after potential exposure and removing them can help prevent infection.

*Borrelia burgdorferi* enters the skin at the site of the tick bite. It may spread in lymph, producing regional adenopathy, or disseminate in blood to organs or other skin sites. The relative paucity of organism in the involved tissue suggests that most manifestations of infection are due to host immune response rather than to the destructive properties of the organisms.

Patients with Lyme disease suffer from a variety of chronic and acute syndromes caused by *Borrelia burgdorferi*. The signs and symptoms of Lyme disease vary over time and between individuals. The characteristic clinical manifestation following the bite of an infected tick is a distinctive skin rash, erythema migrans, which often occurs in conjunction with mild constitutional symptoms. Later stages of Lyme disease may include severe arthritic, neurological, and cardiac manifestations.

The diagnosis of Lyme disease is made by clinical examination combined with evidence of tick bite or exposure in endemic areas, and this usually coincides with evidence of seroreactivity to the organism. Diagnosis of early Lyme disease in a patient with typical erythema migrans in an endemic area does not require laboratory confirmation. Titers of specific antispirochetal antibodies (first IgM, then IgG) can be determined by ELISA or by indirect immunofluorescence, but are not useful before the patient has made antibodies. Confirmation of positive titers by Western blot is also needed. In addition, false- positive results can be high. Thus, testing is best reserved for patients in whom suspicion is high. Moreover, serological testing does not recognize the presence of the spirochete itself, but rather the host's immunological response to the organism following a recent or past infection. Culture of *Borrelia burgdorferi* from blood and other body tissues is possible, but the recovery rate is low, and it may require many weeks before growth of the organism is evident.

The polymerase chain reaction (PCR) provides a sensitive and specific means of detecting the presence of *Borrelia burgdorferi* in clinical specimens, and it has been used successfully to detect *Borrelia burgdorferi* in body fluids including blood. See, e.g., (Benach et al., N. Engl. J. Med. 308: 740–742, 1983); serum (Liebling et al., Arth Rheum 36: 665–675, 1993); cerebral spinal fluid and synovial fluid (Liebling et al., Arth Rheum 36: 665–675, 1993); and in urine (Schmidt et al., Diagn. Microbiol. Infect. Dis. 21: 121–128, 1995). A diagnosis of *Borrelia burgdorferi* infections using a real-time PCR assay is also reported (Schwaiger et al., *Clin. Microbiol. Infect.* 7(9): 461–9, 2001).

SUMMARY OF THE INVENTION

The present invention provides methods and compositions for determining the presence and/or amount of *Borrelia burgdorferi* nucleic acids in a test sample. In particular, substantially purified oligonucleotides for qualitatively and/or quantitatively detecting *Borrelia burgdorferi* nucleic acids in a test sample by amplification methods are described herein. The present invention can provide a specific, sensitive method that can exhibit a broad dynamic range of detection of *Borrelia burgdorferi* nucleic acids.

In various embodiments of the present invention, oligonucleotide primers and probes are used in the methods described herein to provide the *Borrelia burgdorferi* assay. Thus, in certain embodiments, the invention relates to primer sequences that can be used to amplify FlaA gene in the *Borrelia burgdorferi* gene sequence present in a sample. The FlaA gene in the *Borrelia burgdorferi* gene sequence encodes the flagellin protein. In addition, primers can also be used to amplify one or more control nucleic acid sequences. Control amplification primers may contain only control-specific sequences, or may be hybrid primers that can amplify the control sequence(s) while simultaneously introducing FlaA gene sequences into the control amplicon produced. By introducing FlaA gene sequences into the control amplicon, the control can be introduced into test samples and amplified by the same primers used to amplify the target FlaA gene in the *Borrelia burgdorferi* gene sequences, providing a convenient positive control.

In additional embodiments, the invention relates in part to probe nucleic acids that can be conjugated to a detectable label, preferably, a fluorescent dye, and most preferably a dye pair located at the 5' and 3' end of the oligonucleotides. Certain labeled oligonucleotides are described that hybridize to amplified FlaA gene in the *Borrelia burgdorferi* gene sequences, if present, in the sample. Similarly, certain labeled oligonucleotides are described that hybridize to a control amplicon that may have been introduced into the test sample as a positive control.

In a first aspect, the invention relates to one or more substantially purified oligonucleotides having sequences selected from the following group:

5'-TTG CAA ATC TTT TCT CTG GTG-3' (SEQ ID NO:1), a Fla A gene sequence;

5'-AGA ATT AAC TCC GCC TTG AGA-3' (SEQ ID NO:2), a Fla A gene sequence;

5'-CCT TCC TGT TGA ACA CCC TCT TGA AC-3' (SEQ ID NO:3), a probe hybridizing to Fla A gene sequence;

5'-CTT GTA CCA GTT GTA CGG TCC-3' (SEQ ID NO:4), a human placental DNA sequence suitable for use as a primer for internal positive control amplification;

5'-GGT AGC AGC GGT AGA GTT GTA-3' (SEQ ID NO:5)), a human placental DNA sequence suitable for use as a primer for internal positive control amplification; and 5'-ATC ATG ATG TTC AAG TTG TGT TTT GC-3' (SEQ ID NO:6), a human placental DNA sequence suitable for use as a probe for hybridizing to human placental DNA.

In preferred embodiments, one or more of the selected oligonucleotides can be conjugated to a detectable label, preferably a fluorescent dye, and most preferably a dye pair. Particularly preferred oligonucleotide dye conjugates are 5'-[6-carboxyfluorescein(FAM)]-CCT TCC TGT TGA ACA CCC TCT TGA AC-[6-carboxytetramethylrhodamine (TAMRA)]-3' (SEQ ID NO:7); and 5'[2'-Chloro-7'-phenyl-1,4-dichloro-6-carboxyfluorescein (VIC)]-ATC ATG ATG TTC AAG TTG TGT TTT GC-[6-carboxytetramethylrhodamine (TAMRA)]3' (SEQ ID NO:8). These may be used as probes for FlaA gene and human placental DNA, respectively, in methods to detect the presence or amount of specific nucleic acids present in a test sample.

In another aspect, the present invention relates in part to methods that use primers to a sequence unrelated to *Borrelia burgdorferi*, e.g., human placental nucleic acid primers, to produce control amplicons as a positive assay control. In preferred embodiments, oligonucleotides having the sequences 5'-CTT GTA CCA GTT GTA CGG TCC-3' (SEQ ID NO:4) and 5'-GGT AGC AGC GGT AGA GTT GTA-3' (SEQ ID NO:5) are used as primers to amplify a sample of human placental nucleic acid to produce the control amplicons.

In various embodiments, control DNA, e.g., human placental DNA, can be spiked into a sample suspected to contain *Borrelia burgdorferi*, and two sets of primers, one set selected to amplify a control DNA sequence, and a second set selected to amplify a *Borrelia burgdorferi* sequence can be used during the amplification step. In these embodiments, amplification of the control DNA sequence can be detected as a positive control. If the control DNA is added prior to amplification, the positive control can signal successful amplification in samples negative for *Borrelia burgdorferi*. Alternatively, if the control DNA is added prior to nucleic acid isolation (which may occur prior to amplification), the positive control can signal both successful nucleic acid isolation and successful amplification.

In certain embodiments, FlaA-human placental hybrid amplicons can be prepared and purified for use in *Borrelia burgdorferi* assays. In these embodiments, hybrid amplicon nucleic acid can be prepared by including FlaA sequences in the control primers described above. These hybrid amplicons can then be introduced into a sample to be analyzed for the presence or amount of FlaA gene in the *Borrelia burgdorferi* gene sequence. Because of the flanking FlaA gene sequences present in the hybrid amplicon, primers can be selected that can amplify both the hybrid nucleic acid added, as well as any FlaA gene in the *Borrelia burgdorferi* gene sequence present in the sample. Depending on the timing at which the hybrid nucleic acid is introduced into the sample, the hybrid nucleic acid can serve as a positive control for nucleic acid extraction from the sample, and/or for an FlaA amplification reaction.

In another aspect, the present invention relates in part to methods for detecting the presence or amount of FlaA gene in the *Borrelia burgdorferi* gene sequence present in a test sample. The FlaA gene encodes the flagellin protein in the *Borrelia burgdorferi* gene sequence. These methods preferably comprise amplifying FlaA gene sequence if present in said sample using a pair of oligonucleotide primers; hybridizing said amplified FlaA gene with an oligonucleotide probe; and detecting a signal from said hybridized FlaA, wherein the signal is related to the presence or amount of FlaA gene in the *Borrelia burgdorferi* gene sequence in the test sample.

In various preferred embodiments, the oligonucleotide primers have the sequences 5'-TTG CAA ATC TTT TCT CTG GTG-3' (SEQ ID NO:1) and 5'-AGA ATT AAC TCC GCC TTG AGA-3' (SEQ ID NO:2), respectively; these primers hybridize to flanking regions on the FlaA gene. One of the primers anneals to base pairs 581–601 (from GenBank Accession# x15661) on the FlaA gene; the another anneals to base pairs 688–708 (from GenBank Accession# x15661) on the FlaA gene; the oligonucleotide probe can have the sequence 5'-CCT TCC TGT TGA ACA CCC TCT TGA AC-3' (SEQ ID NO:3); which corresponds to base pairs 631–656 (from GenBank Accession# x15661); the oligonucleotide probe comprises a detectable label; the oligonucleotide probe has the sequence 5'(FAM)-CCT TCC TGT TGA ACA CCC TCT TGA AC-(TAMRA)3' (SEQ ID NO:7); a positive control nucleic acid is introduced into the test sample prior to amplification of FlaA sequences; the positive control nucleic acid is human placental DNA; oligonucleotides having the sequences 5'- CTT GTA CCA GTT GTA CGG TCC-3' (SEQ ID NO:4) and 5'-GGT AGC AGC GGT AGA GTT GTA-3'(SEQ ID NO:5) are used as primers to amplify a sample of human placental nucleic acid to produce positive control nucleic acid; the positive control nucleic acid is detectable using an oligonucleotide probe having the sequence 5'-ATC ATG ATG TTC AAG TTG TGT TTT GC-3' (SEQ ID NO:6); and/or the positive control nucleic acid is detected using an oligonucleotide probe having the sequence 5'(VIC)-ATC ATG ATG TTC AAG TTG TGT TTT GC-(TAMRA)3' (SEQ ID NO:8).

In yet another aspect of the present invention, a "real time PCR" assay providing dynamic fluorescence detection of amplified FlaA products produced in a PCR amplification reaction is described. During PCR, the amplified products hybridize to probe nucleic acids, which are labeled with both a reporter dye and a quencher dye. When these two dyes are in close proximity, i.e. both are present in an intact probe oligonucleotide, the fluorescence of the reporter dye is suppressed. However, a polymerase, such as AmpliTaq Gold™, having 5'-3' nuclease activity can be provided in the PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequencing apparatus, the fluorescent signal produced by the reporter dye is detected and/or quantified. The increase in fluorescence is a direct consequence of amplification of target nucleic acids during PCR.

In various preferred embodiments, the oligonucleotide primers used in the PCR amplification have the sequences 5'-TTG CAA ATC TTT TCT CTG GTG-3' (SEQ ID NO:1) and 5'-AGA ATT AAC TCC GCC TTG AGA-3' (SEQ ID NO:2); the reporter dye is FAM and the quencher dye is TAMRA; the FlaA oligonucleotide probe has the sequence 5'(FAM)-CCT TCC TGT TGA ACA CCC TCT TGA AC-(TAMRA)3' (SEQ ID NO:7); a positive control nucleic acid is introduced into the test sample prior to PCR amplification of FlaA gene sequences; the positive control nucleic acid is human placental DNA; oligonucleotides having the sequences 5'-CTT GTA CCA GTT GTA CGG TCC-3' (SEQ ID NO:4) and 5'-GGT AGC AGC GGT AGA GTT GTA-3' (SEQ ID NO:5) are used as primers to amplify a sample of human placental nucleic acid to produce positive control nucleic acid; the positive control nucleic acid is amplified by the same primers used to amplify the FlaA gene sequences; the reporter dye is VIC and the quencher dye is TAMRA; and/or the positive control nucleic acid is detected using an oligonucleotide probe having the sequence 5'(VIC)-ATC ATG ATG TTC AAG TTG TGT TTT GC-(TAMRA)3' (SEQ ID NO:8).

In yet another aspect, the methods and compositions for detecting and/or quantifying *Borrelia burgdorferi* gene of the present invention can be used for designing a treatment regimen. In particular, the detection of the presence or amount of *Borrelia burgdorferi* nucleic acid in a biological sample following a selected treatment(s) can be used to assess the success or lack thereof in the treatment regimen. The present invention can also be used to compare the relative presence or amount of *Borrelia burgdorferi* nucleic acids in a patient before and after such a treatment regimen. Similarly, methods and compositions described herein can be used for screening therapeutic compounds. In particular, the quantitative detection of the presence or amount of *Borrelia burgdorferi* nucleic acids in a biological sample following administration of one or more compounds can be used to assess therapeutic efficacy. The present invention can also be used to compare the relative presence or amount of *Borrelia burgdorferi* nucleic acids in a patient before and after administration of one or more compounds.

In another aspect, the present invention relates in part to kits comprising sufficient materials for performing one or more methods described herein. In preferred embodiments, a kit includes one or more materials selected from the following group in an amount sufficient to perform at least one *Borrelia burgdorferi* assay: Oligonucleotide primers having the sequences 5'-TTG CAA ATC TTT TCT CTG GTG-3' (SEQ ID NO:1) and 5'-AGA ATT AAC TCC GCC TTG AGA-3' (SEQ ID NO:2); an oligonucleotide probe having the sequence 5'-CCT TCC TGT TGA ACA CCC TCT TGA AC-3' (SEQ ID NO:3); an oligonucleotide probe having the sequence 5'(FAM)-CCT TCC TGT TGA ACA CCC TCT TGA AC-(TAMRA)3' (SEQ ID NO:7); a positive control nucleic acid to be introduced into a test sample prior to amplification of FlaA gene sequences; a positive control nucleic acid that is human placental DNA; oligonucleotides having the sequences 5'-CTT GTA CCA GTT GTA CGG TCC-3' (SEQ ID NO:4) and 5'-GGT AGC AGC GGT AGA GTT GTA-3' (SEQ ID NO:5) to be used as primers to amplify a sample of human placental nucleic acid to produce positive control nucleic acid; a positive control nucleic acid that is detectable using an oligonucleotide probe having the sequence 5'-ATC ATG ATG TTC AAG TTG TGT TTT GC-3' (SEQ ID NO:6); a positive control nucleic acid that is detected using an oligonucleotide probe having the sequence 5'(VIC)-ATC ATG ATG TTC AAG TTG TGT TTT GC-(TAMRA)3' (SEQ ID NO:8); and/or an oligonucleotide probe having the sequence 5'(VIC)-ATC ATG ATG TTC AAG TTG TGT TTT GC-(TAMRA)3' (SEQ ID NO:8).

DETAILED DESCRIPTION OF THE PREFERRED EMBODIMENTS

The present invention provides methods and compositions for the rapid and sensitive determination of *Borrelia burgdorferi* nucleic acids in test samples. In particular, oligonucleotide probes and primers are described that can be used for quantitatively or qualitatively detecting FlaA gene sequence encoding the flagellin protein on the *Borrelia burgdorferi* gene sequence in a sample. The present invention also provides primers and probes for generating and detecting control nucleic acid sequences that provide a convenient method for assessing internal quality control of the *Borrelia burgdorferi* assay.

As used herein, the term "FlaA-human placental nucleic acid hybrids" refers to chimeric nucleic acid molecules containing both FlaA gene sequences and human placental nucleic acids sequences. Preferred FlaA-human placental hybrids comprise a core sequence from human placental DNA, flanked by FlaA sequences having sufficient length to hybridize to amplification primers. Preferably, the FlaA-human placental hybrid comprises at least 3 consecutive bases from an FlaA sequence, more preferably at least 5 consecutive bases from an FlaA sequence, even more preferably at least 10 consecutive bases from an FlaA sequence, and most preferably at least 20 consecutive bases from an FlaA sequence.

As used herein, the term "purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, the term "oligonucleotides" refers to a short polymer composed of deoxyribonucleotides, ribonucleotides or any combination thereof. These oligonucleotides are at least 9 nucleotides in length, preferably 20 to 50 nucleotide long, with 21 to 26 nucleotides being the most common. In certain embodiments, the oligonucleotides are jointed together with a detectable label.

As used herein, the term "*Borrelia burgdorferi* nucleic acids" and/or *Borrelia burgdorferi* gene sequence refer to DNA and/or RNA comprising a contiguous sequence from *Borrelia burgdorferi* genome, or the complement thereof. *Borrelia burgdorferi* nucleic acids and/or gene sequence may be *Borrelia burgdorferi* genomic DNA, *Borrelia burgdorferi* messenger RNA, or the complement of these sources, obtained by any method including obtaining the nucleic acid from a biological source, synthesizing the nucleic acid in vitro, or amplifying the nucleic acid by any method known in the art.

As used herein, the term "hybridize" refers to process that two complementary nucleic acid strands anneal to each other under appropriately stringent conditions. Hybridizations are typically and preferably conducted with probe-length nucleic acid molecules, preferably 20–100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/ml sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "amplify" with respect to nucleic acid sequences refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13–20; Wharam et al., Nucleic Acids Res. Jun. 1, 2001;29(11):E54–E54; Hafner et al., Biotechniques April 2001;30(4):852–6, 858, 860 passim; Zhong et al., Biotechniques April 2001;30(4):852–6, 858, 860 passim.

As used herein, the term "test sample" refers to any liquid or solid material believed to comprise Borrelia burgdorferi nucleic acids. In preferred embodiments, a test sample is obtained from a biological source, such as cells in culture or a tissue sample from an animal, most preferably, a human. Preferred sample tissues of the instant invention include, but are not limited to, plasma, serum, whole blood, blood cells, lymphatic fluid, cerebrospinal fluid, synovial fluid, urine, saliva, and skin or other organs (e.g. biopsy material). The term "patient sample" as used herein refers to a tissue sample obtained from a human seeking diagnosis or treatment of a disease related to a Borrelia burgdorferi infection.

The term "detectable label" as used herein refers to a composition or moiety that is detectable by spectroscopic, photochemical, biochemical, immunochemical, electromagnetic, radiochemical, or chemical means such as fluorescence, chemifluoresence, or chemiluminescence, or any other appropriate means. Preferred detectable labels are fluorescent dye molecules, or fluorochromes, such fluorescein, phycoerythrin, CY3, CY5, allophycocyanine, Texas Red, peridenin chlorophyll, cyanine, FAM, JOE, TAMRA, tandem conjugates such as phycoerythrin-CY5, and the like. These examples are not meant to be limiting. Methods and compositions for detectably labeling molecules, such as oligonucleotides, PNA-DNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

The term "fluorochrome" as used herein refers to a molecule that absorbs a quantum of electromagnetic radiation at one wavelength, and emits one or more photons at a different, typically longer, wavelength in response. In preferred embodiments, a fluorochrome can be a member of a pair of physically linked fluorochromes that exhibit fluorescence energy transfer. An energy transfer pair may be excited by a quantum of electromagnetic radiation at a wavelength at which the donor fluorochrome is excited; however, fluorescence from the donor fluorochrome that would be expected in the absence of the acceptor is quenched at least in part, and emission at an emission wavelength of the acceptor fluorochrome is observed.

In particularly preferred embodiments, a fluorochrome is one member of a physically linked "molecular beacon" pair. In these embodiments, the molecular beacon pair may be excited by a quantum of electromagnetic radiation at a wavelength at which a first fluorochrome member of the pair is excited; however, fluorescence from the first fluorochrome that would be expected in the absence of the second fluorochrome is quenched at least in part. Unlike energy transfer pairs, however, emission at an emission wavelength of the acceptor fluorochrome is not observed. Thus, these labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

The term "linker" as used herein refers to one or more chemical bonds or a chemical group used to link one moiety to another, serving as a divalent bridge, where it provides a group between two other chemical moieties.

Sample Preparation

The presence or amount of Borrelia burgdorferi nucleic acids in a sample can be determined by amplifying one or more target regions, such as nucleotides in the FlaA gene, within the Borrelia burgdorferi genome. Thus, any liquid or solid material believed to comprise Borrelia burgdorferi nucleic acids can be an appropriate sample. Preferred sample tissues include plasma, serum, whole blood, blood cells, lymphatic fluid, cerebral spinal fluid, synovial fluid and others.

Such samples will often be taken from patients suspected of having Borrelia burgdorferi infection, or having a clinical manifestations of Lyme disease. Nucleic acids representing Borrelia burgdorferi may be extracted from tissue samples. Various commercial nucleic acid purification/extraction systems and kits are known to the skilled artisan, and used to isolate Borrelia burgdorferi nucleic acids from samples. For example, the MagNA Pure automated extraction system may be used for all specimen types. The MagNA Pure system is used for simultaneous extraction of all specimens with a single protocol using the system's MagNA Pure LC DNA isolation Kit I.

Amplification of Borrelia burgdorferi Nucleic Acids

Target samples or isolated nucleic acids may be amplified by various methods known to the skilled artisan. Preferably, PCR is used to amplify Borrelia burgdorferi nucleic acids. In this method, two or more oligonucleotide primers that flank and bind to opposite strands of a target sequence are repetitively annealed to their complementary sequences, extended by a DNA polymerase, and heat denatured, resulting in exponential amplification of the target nucleic acid sequences. The skilled artisan is capable of designing and preparing primers that are appropriate for amplifying a target sequence. In preferred embodiment of the instant invention, primers are designed for amplifying all or a part of the FlaA gene of Borrelia burgdorferi. These primers hybridize to flanking regions on the FlaA gene encoding the flagellin protein. The primers amplify the regions of 581–708 bp on the FlaA gene (from GenBank accession number x15661). Cycling parameters can be varied, depending on the length of nucleic acids to be extended.

Hybridization Probes With a Detectable Label

Oligonucleotide probes complementary and hybridizing to the amplified target nucleic acids may be conjugated to a detectable label. Preferably, the detectable label is a fluorescent dye. Particularly preferred are detectable labels known as "molecular beacons." These labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

Molecular beacons can be utilized during PCR, for example, by using a DNA polymerase that cleaves a probe nucleic acid if it is bound specifically to the target nucleic acid sequence. Quantitative real-time PCR is based on detection of a fluorescent signal produced proportionally during the amplification of a PCR product. A probe is designed to anneal to the target sequence between the traditional forward and reverse primers. The probe is labeled at the 5' end with a reporter fluorochrome, and a quencher fluorochrome is added at any other position (or at the 3' end). The probe is designed to have a higher $T_m$ than the primers. As long as both fluorochromes are on the probe, the quencher molecule stops all fluorescence by the reporter. However, as Taq polymerase extends the primer, the intrinsic 5' to 3' nuclease activity of Taq degrades the probe, releasing the reporter fluorochrome. The amount of fluorescence released during the amplification cycle is proportional to the amount of product generated in each cycle. See, e.g., van Schie et al., *Biotechniques* 29: 1296–1300 (2000).

Methods for attaching detectable labels are well known in the art. See, e.g., Chu et al., Methods Mol. Biol. 26, 145–165 (1994); Hileman et al., Bioconjug. Chem. 5, 436–444 (1994).

In preferred embodiment of the instant invention, the oligonucleotide probe hybridizes to the amplified FlaA gene sequence. The probe corresponds to 631–656 bp of FlaA gene (from GenBank accession number x15661), and is attached to a pair of detectable labels.

Preparation of an Internal Control

As a quality control measure, an internal amplification control may be included in one or more samples to be extracted and amplified. While human placental nucleic acid control sequences are described herein, the skilled artisan will understand that any detectable sequence that is not derived from *Borrelia burgdorferi* can be used as the control sequence. A control sequence can be produced synthetically, but is preferably produced by amplifying the control sequence, e.g., human placental DNA, using a pair of human placental primer sequences. In particularly preferred embodiments, a control primer is a hybrid nucleic acid comprising human placental sequence flanked by FlaA primer target sequences. Sequences amplified using these hybrid nucleic acids comprise a human placental sequence flanked by sequences that hybridize to FlaA primer sequences These controls can be mixed with sample (or purified nucleic acids isolated from the sample), and amplified with sample nucleic acids using a pair of FlaA primers. If PCR amplification is successful, the internal amplification control amplicons can then be detected and differentiated from FlaA sequences using a probe to the human placental sequence. Additionally, if included in the sample prior to purification of nucleic acids, the control sequences can also act as a positive purification control.

*Borrelia burgdorferi* Assay

In preferred embodiments, the FlaA gene specific primers are shown in SEQ ID:1 and SEQ ID:2, although the skilled artisan will understand that other probes may be used. Stock *Borrelia burgdorferi* standard curve dilutions may be run simultaneously. The methods described herein can provide qualitative and quantitative results up to about 5,000 *Borrelia burgdorferi* organisms per reaction.

To minimize the potential for cross contamination, reagent and master mix preparation, specimen processing and PCR setup, amplification and detection are conducted in physical separated areas.

EXAMPLES

Example 1

Sample Collection and Preparation

Urine: Midstream urine specimen (5 ml) is stable at 4–8° C. for 14 days before shipping. The frozen urine specimen can be stored at –20° C. for up to 2 months.

Blood: Peripheral blood was collected in sterile tubes, either in yellow top (ACD) tubes or lavender top (EDTA) tubes. Upon receipt in the laboratory, the blood specimens can be stored at 2–8° C. for a maximum of 7 days.

CSF or Synovial Fluid: The amount of CSF or synovial fluid should be more than 0.2 ml, prefer 2–3 ml. Such specimens can be stored at –20° C. for 3 months, or at 2–8° C. for a maximum of 30 days.

Ticks: The should specimens are accepted in 70% ethanol or ethanol-wet tissue, but not in formalin. A list of ticks that are acceptable for PCR is as follows: (1) known tick vectors of Lyme disease *Ixodes scapularis* (dammini); *Ixodes pacificus* (Northeast and Midwest U.S); *Ixodes vicinus* (Europe); *Ixodes persulcatus* (Asia); and (2) Implicated tick vectors of Lyme disease: *Amblyomama americanum* (secondary vector); *Ixodes angustus* (possible vector of *Borrelia burgdorferi*); *Ixodes albipictus; Ixodes spinipal/neotomae* (not seen on humans); and *Dermacentor variabils* (considered as incompetent vector).

High and Low Positive Sample Preparation: The high positive sample preparation (HiPSP) refers to a sample containing 5,000 *Borrelia burgdorferi* organisms per reaction. The low positive sample preparation (LoPSP) refers to a sample containing 100 *Borrelia Burdorferi* organisms per reaction. The negative sample preparation was sterile PBS solution. An internal positive amplification control (IPC+) was also included with each sample. The preparation of HiPSP and LoPSP are described as follows:

*Borrelia burgdorferi* were cultured as follows: organisms are grown in BSKH media (Sigma Cat. # 3528) supplemented with 10% rabbit serum (Sigma Cat.# R7136). Prior to adding the serum to the media, the serum should be heat inactivated at 56–60° C. for 30 min. To initiate a culture, frozen glycerol stocks stored at –70° C. are used. The growth media should be freshly prepared before each use, and contain 1 ml of rabbit serum and 9 ml of BSKH medium. A vial frozen stock culture was thawed, and 100 $\mu$l aliquot was removed to the 10 ml freshly prepared growth media in a 15 ml screw cap tube, screwed on cap tightly. The growth media with stock culture was incubated at 37° C. without agitation. Bacteria from frozen stocks will routinely grow in 3 to 5 days. The passage number of the culture upon each subculture should be recorded. For example, if the frozen stock is passage 8, the new culture will be passage 9, and a subculture from the new culture will be passage 10.

To make a frozen stock of *Borrelia burgdorferi*, organisms were grown to a high density (approximately $10^8$ per ml); 2 ml of sterile glycerol (50%, Sigma Cat#G2025, dilute 1:1 with water and autoclave) is added to the 10 ml of culture. The culture was frozen at –70° C. or lower.

*Borrelia burgdorferi* were enumerated by counting organisms in a wet mount slide preparation using darkfield microscopy. The 40× objective on an Olympus microscope with a darkfield condenser was utilized for this procedure. A *Borrelia burgdorferi* wetmount was prepared by adding 22 $\mu$l of a resuspended culture to a slide. The liquid was then covered by a 22×40 mm coverslip. The slide was viewed, and organisms were counted. To determine the number of organism per ml, all organisms in ten different fields were counted, and the numbers were averaged. The average count was multiplied by $2.2 \times 10^5$ to give the number of organisms per ml.

If there are too many organisms to accurately count, a dilution of organisms can be made, and this dilution factor is taken into consideration when making the final count. For example, if a 1 in 10 dilution is made, the final count is (average number per field)$\times(2.2 \times 10^5) \times 10$.

Once organisms were been quantitated, the organisms were diluted in PBS such that the final concentration is $1 \times 10^6$ organisms per ml. The organisms were washed by pelleting 1.0 ml of diluted organisms in a microcentrifuige at 10,000×g or greater (i.e. 13,000 rpm in labnet centrifuge) for 10 min. The supernatant was then removed, and the pellet was resuspended in 1.0 ml of PBS. The wash step may be repeated twice The final concentration of the HiPSP stock solution should be diluted to $1 \times 10^6$ organisms/ml such that one microliter contains 1000 organisms (1,000 organisms/ml). This stock solution can be stored at −20° C. or lower.

The final concentration of the LoPSP stock solution should be diluted to $2 \times 10^4$ organisms/ml such that a one microliter contains 20 organisms (20 organisms/ml). This is accomplished by making a 1:50 dilution of the HiPSP. This stock solution can be stored at −20° C. or lower.

An example of calculating the concentration of HiPSP and LoPSP is as follows: if the average count per field of view is 25 organisms, there are: $25 \times (2.2 \times 10^5) = 5.5 \times 10^6$ organisms per ml. To obtain a HiPSP stock solution, which is $1 \times 10^6$ organisms/ml, it will require a 1:5.5 dilution ($5.5 \times 10^6/1 \times 10^6 = 5.5$). To obtain a LoPSP stock solution, which is $2 \times 10^4$ organisms/ml, it will require a 1:50 dilution of the $1 \times 10^6$ HiPSP stock solution.

Once appropriate stock dilutions were made, individual PSP aliquots were made to provide HiPSP or LoPSP stock solutions Each of the HiPSP aliquots labeled as "*Borrelia burgdorferi* HiPSP" contained 5000 organisms/200 μl PBS), and each of the LoPSP aliquots labeled as "*Borrelia burgdorferi* LoPSP" contained 100 organisms/200 μl PBS. All of the aliquots were stored at −20° C. PBS with no organisms added was aliquoted in volumes of 0.5 ml and labeled as "*Borrelia burgdorferi* Negative Sample Prep (VSP)."

Example 2

MagNA Pure Extraction of *Borrelia burgdorferi* DNA

Pre-extraction processing of specimens: Specimens should be prepared under a biohood. All instruments including pipettors, pipettes, bulbs, etc. should be used only for sample preparation and should be maintained in the hood or clean area at all times.

For pre-extraction processing of blood, CSF, SF, and urine samples and controls, a vial of HiPSP, LoPSP, NSP and a sample specimen were thawed and vortexed for 5 seconds, and then 200 μl of each was placed into their corresponding position in a MagNA Pure sample cartridge.

For ticks, the organisms were processed as follows: pipette 50 μl of PBS into each sample tube, place tick in appropriately labeled tubes, cut tick into pieces with scissors, and add additional 300 μl PBS; add 20 μl 10% SDS and 15 μl Proteinase K solution (15 μg/μl) to each sample tube and each control tube, vortexing for 5 seconds. The tubes were incubated at 65° C. for 30 min in a heat block, centrifuged at 13,500 rpm in Labnet centrifuge (or equivalent) for 5 seconds, and then 200 μl of each sample was transferred into its corresponding position in the MagNA Pure sample cartridge.

The MagNA Pure automated extraction system was used for all specimen types. The system's MagNA Pure LC DNA isolation Kit I allows for simultaneous extraction of all specimens with a single protocol.

Before running MagNA Pure software, the workstation should be decontaminated by wiping the surface with a paper towel soaked in 10% bleach. MagNA Pure Proteinase K reagent was prepared by dissolving each vial of Proteinase K (vial 4, white cap) in 5.0 ml of elution butter (vial 6, yellow cap) provided by the system, followed by vortexing for 5 seconds. One vial of Proteinase K may be used for 32 isolations, and the unused solution can be stored at 2–8° C. for up to 1 month. The magnetic glass particles (MGP) Ha were dispensed to the reagent tub after vortexing for 10 seconds. The purification process was run in accordance with the protocol provided by the system.

Example 3

Preparation for *Borrelia burgdorferi* Real-Time PCR and Fluorogenic Probe Hybridization A master mixture of reagents for performing PCR, and further hybridization with the fluorogenic probe was prepared as shown in Table 1. The mixture was dispensed in 1.0 ml aliquots and stored at −20° C. The fluorescein dyes useful in the instant invention include 6-carboxyfluorescein (6-FAM), 5'-dichloro-6-carboxyrhodamine (JOE), and 2'-chloro-7'-phenyl-1,4-dichloro-6-carboxyfluorescein (VIC). Another preferred class of labels include quencher moieties. The emission spectra of a quencher moiety overlaps with a proximal intramolecular or intermolecular fluorescent dye such that the fluorescence of the fluorescent dye is substantially diminished, or quenched, by fluorescence resonance energy transfer (FRET). Oligonucleotides which are intramolecularly labeled with both fluorescent dye and quencher moieties are useful in nucleic acid hybridization assays, e.g. the "Taqman" exonuclease-cleavage PCR assay (U.S. Pat. Nos. 5,723,591; 5,538,848). The quencher moieties used in the instant invention include but not limited to tetramethyl-6-carboxyrhodamine (TAMRA).

The primers were obtained from Operon (Alameda, Calif.). Probes labeled with FAM and TAMRA were obtained from Operon. Probes labeled with VIC and TAMRA were obtained from Applied Biosystems (Foster City, Calif.). Both primers and probes were HPLC purified and shipped as a lyophilized (dry) powder. Each was brought to a concentration of 100 pmol/1.

The internal positive control DNA template was human placental DNA (Sigma #D-7011, 1 mg), stored at 2–8° C. A stock solution (50 mg/ml) was prepared as follows: DNA was transferred to a 50 ml sterile, conical tube, and 20 ml of TE buffer (10 mM Tris, 1 mM EDTA, pH 8) was added. The solution was rocked overnight on a mechanical rocker at 15–30° C. The stock solution was stored at −20° C. for 1 year.

TABLE 1

Lyme Taqman Mastermix preparation

| Reagents | μL/reaction | Unit of Measure 1000 rxn | Final Concentration per reaction |
|---|---|---|---|
| Sterile Nuclease Free Water | 19.645 | 19.645 ml | |
| 10xPCR Buffer | 5 | 5 ml | 1 x |
| Rox solution (100 μM) | 0.15 | 150 μl | 0.3 μM |
| 100 mM dATP | 0.1 | 100 μl | 100 μM |
| 100 mM dCTP | 0.1 | 100 μl | 100 μM |
| 100 mM dGTP | 0.1 | 100 μl | 100 μM |
| 20 mM dUTP | 1.0 | 1.0 ml | 200 μM |
| 25 mM $MgCl_2$ | 12 | 12 ml | 6 mM |
| FLA-F primer (100 μM) | 0.2 | 0.2 ml | 400 nM |

TABLE 1-continued Lyme Taqman Mastermix preparation

| Reagents | μL/reaction | Unit of Measure 1000 rxn | Final Concentration per reaction |
|---|---|---|---|
| FLA-R primer (100 μM) | 0.2 | 0.2 ml | 400 nM |
| IPC-F Primer (100 μM) | 0.015 | 15 μl | 30 nM |
| IPC-R Primer (100 μM) | 0.015 | 15 μl | 30 nM |
| FLA-probe (100 μM) | 0.05 | 50 μl | 100 nM |
| IPC-probe (100 μM) | 0.04 | 40 μl | 80 nM |
| Human placental DNA (50 ng/ml) | 0.02 | 20 μl | 1 ng |
| Total | 38.5 μl | 38.5 ml | |

In the mixture, the FLA-F primer used was 5'-TTG CAA ATC TTT TCT CTG GTG-3' (SEQ ID NO:1), and FLA-R primer was 5'-AGA ATT AAC TCC GCC TTG AGA-3' (SEQ ID NO:2). The FLA-probe was 5'[FAM]-CCT TCC TGT TGA ACA CCC TCT TGA AC-[TAMRA]3' (SEQ ID NO:7). The IRC-F primer was 5'-CTT GTA CCA GTT GTA CGG TCC-3' (SEQ ID NO:4), and IRC-R primer was 5'-GGT AGC AGC GGT AGA GTT GTA-3' (SEQ ID NO:5). The IRC probe was 5'-[VIC]-ATC ATG ATG TTC AAG TTG TGT TTT GC-[TAMRA]3' (SEQ ID NO:8).

The Lyme Taqman mastermix was aliquoted in 1 ml per vial, labeled as "Lyme Taqman Mastermix."

To perform the real time PCR, aliquots of the Lyme Taqman Mastermix were thawed and mixed with 26 μl of AmpliTaq Gold and 13 μl of AmpErase (UNG, 1U/μL) (to 1 vial of mastermix), inverting 10 times to mix.

Real time PCR was performed in a 96 well optical plate and the signals were detected using the ABI 7700 Sequence Detector. 40 μl of mastermix was loaded into all appropriate wells using a repeat pipettor. 10 μl of samples were also loaded and mixed with mastermix by up and down pipetting (2×). The plate was then tightly sealed with the optical sealing card using a sealing tool and the side tabs were pulled off with a quick motion outward. The wells in the plate were examined and gently tapped if bubbles were present in the bottom of the wells. The plate was then transferred to the ABI 7700 sequence detector. A pressure pad was placed on top of the plate and a heat block lid was placed onto the top of the plate and screwed down.

The total reaction volume was 50 μl. The thermocycler conditions were as follows: stage 1: 50° C. for 2 minutes; stage 2: 95° C. for 10 minutes; stage 3: 43 cycles of 95° C. for 15 seconds and 60° C. for 1 minute. The operation of the Taqman 7700 was as described in the manual.

Example 4

Data Analysis and Reporting

An assay flowchart for *Borrelia burgdorferi* DNA quantitative PCR is shown in FIG. 1. An average threshold cycle (Ct) value will be assigned for each well. The Ct value indicates the cycle at which exponential growth of a PCR product is occurring. If the Ct value is 43, it means that no amplification of the target was achieved. If a well has a Ct value under 43, the target has been amplified, and the PCR is thus considered to be positive.

The Ct value for the HiPSP control will generally be approximately 25.00 and the LoPSP control should have a Ct value of approximately 32.00. The NSP should have a Ct value of 43.00.

All assay controls should be examined prior to interpretation of clinical results. If the controls are not valid, the clinical samples should not be interpreted. All positive specimen controls must be positive (i.e. have Ct value below 43) for the assay to be valid.

A positive internal control (IPC) was included with every sample. All negative samples should have positive amplification of the IPC in order for the result to be valid.

In summary, the detection of *Borrelia burgdorferi* DNA is based upon the amplification of a specific flagellin gene sequence by PCR. It could detect flagellin gene on the *Borrelia burgdorferi* genome, thus monitor therapy and predict the success of antibacterial therapy.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A method for producing an oligonucleotide that is a hybrid of human placental DNA with FlaA nucleic acid sequence, comprising:

amplifying human placental DNA using a pair of oligonucleotide primers having the sequences set forth in SEQ ID NO:4 and SEQ ID NO:5, wherein said primers each further contain a terminal FlaA nucleic acid sequence comprising 5 or more contiguous nucleotides selected from 5'-TTG CAA ATC TTT TCT CTG GTG-3' (SEQ ID NO:1) or 5'-AGA ATT AAC TCC GCC TTG AGA-3' (SEQ ID NO:2) to provide a plurality of human placental-FlaA nucleic acid hybrid amplicons; and purifyng the human placental-FlaA nucleic acid hybrid amplicons.

* * * * *